United States Patent
Ao et al.

(10) Patent No.: US 12,239,297 B2
(45) Date of Patent: Mar. 4, 2025

(54) VIDEO LARYNGOSCOPE WITH GUIDED DECONTAMINATION DEVICE

(71) Applicant: Hushan Ao, Beijing (CN)

(72) Inventors: Hushan Ao, Beijing (CN); Da Ha, Beijing (CN); Yi Qiu, Beijing (CN); Xizhe Zhang, Beijing (CN); Yi Sun, Beijing (CN); YuHua Gong, Beijing (CN); Rina Wu, Beijing (CN); Haixia Shi, Beijing (CN); Ni Shu, Beijing (CN)

(73) Assignee: Hushan Ao, Beijing (CN)

( * ) Notice: Subject to any disclaimer, the term of this patent is extended or adjusted under 35 U.S.C. 154(b) by 0 days.

(21) Appl. No.: 18/569,786

(22) PCT Filed: Jun. 21, 2022

(86) PCT No.: PCT/CN2022/100002
§ 371 (c)(1),
(2) Date: Dec. 13, 2023

(87) PCT Pub. No.: WO2023/005507
PCT Pub. Date: Feb. 2, 2023

(65) Prior Publication Data
US 2024/0260824 A1    Aug. 8, 2024

(30) Foreign Application Priority Data
Jul. 26, 2021   (CN) .......................... 202110841293.6

(51) Int. Cl.
*A61B 1/00*    (2006.01)
*A61B 1/05*    (2006.01)
(Continued)

(52) U.S. Cl.
CPC .......... *A61B 1/126* (2013.01); *A61B 1/00052* (2013.01); *A61B 1/05* (2013.01); *A61B 1/0676* (2013.01); *A61B 1/267* (2013.01)

(58) Field of Classification Search
CPC ....... A61B 1/126; A61B 1/00052; A61B 1/05; A61B 1/0676; A61B 1/267; A61B 1/127
(Continued)

(56) References Cited

U.S. PATENT DOCUMENTS 11,717,146 B2 *   8/2023   Pellerin De Beauvais ..................
                                                              A61B 1/05
                                                              600/190
2012/0101338 A1 * 4/2012   O'Prey .................. A61B 1/126
                                                              600/157
(Continued)

FOREIGN PATENT DOCUMENTS

CN    105212884 A    1/2016
CN    111150365 A    5/2020
(Continued)

OTHER PUBLICATIONS

Jan. 28, 2023 Notification to Grant Patent Right issued in Chinese Patent Application No. 202110841293.6.

*Primary Examiner* — John P Leubecker
*Assistant Examiner* — Li-Ting Song
(74) *Attorney, Agent, or Firm* — Oliff PLC

(57) ABSTRACT

A video laryngoscope with a guided decontamination device includes a laryngoscope handle and a video laryngoscope blade. The front end of the video laryngoscope blade is equipped with a light source and a camera. The guided decontamination device included is composed of a guide tube and a decontamination rod. The guide tube is fixed on the outer wall of the laryngoscope handle, and has its guiding angle in parallel to the end faces of the camera and the light source at the front end of the laryngoscope blade.

(Continued)

The decontamination rod comes into a sliding fit with the guide tube, runs out from the bottom of the guide tube upwards, and has its front end bent to form a decontamination scraper rod. The decontamination scraper rod comes into a tight fit with the end faces of the light source and the camera at the front end of the laryngoscope blade.

9 Claims, 4 Drawing Sheets

(51) Int. Cl.
*A61B 1/06* (2006.01)
*A61B 1/12* (2006.01)
*A61B 1/267* (2006.01)

(58) Field of Classification Search
USPC .......................................................... 600/185
See application file for complete search history.

(56) References Cited

U.S. PATENT DOCUMENTS

| | | | |
|---|---|---|---|
| 2023/0148850 A1* | 5/2023 | Fouts | A61B 1/00119 600/109 |
| 2023/0255465 A1* | 8/2023 | Gaffney, II | A61B 1/00101 600/188 |

FOREIGN PATENT DOCUMENTS

| | | | | |
|---|---|---|---|---|
| CN | 211883729 U | 11/2020 | | |
| CN | 213309594 U | 6/2021 | | |
| WO | WO-2021121035 A1 * | 6/2021 | | A61B 1/04 |

* cited by examiner

VIDEO LARYNGOSCOPE WITH GUIDED DECONTAMINATION DEVICE

FIELD OF THE INVENTION

The invention relates to a medical instrument, in particular to a video laryngoscope with a guided decontamination device, used for clinically lifting the epiglottis of a patient to expose the glottis, and guiding medical staff to accurately perform airway intubation for anesthesia or emergency use, and also used for oral examination and treatment.

BACKGROUND OF THE INVENTION

In 2001, Canadians invented video laryngoscopes. Technically, a video laryngoscope is provided with a camera at the front end of a laryngoscope blade to capture airway images, and the captured images are displayed on a display above a laryngoscope handle so that an operator can directly observe the airway images through the video display. The emergence of video laryngoscopes is a revolutionary technological advancement in airway tools. The video laryngoscopes can well expose glottises to expand the vision of anesthesia and emergency doctors, thereby greatly improving the success rate of tracheal intubation. However, if the camera of a video laryngoscope is contaminated and blocked simply by a drop of blood or secretion from oropharynx, the video laryngoscope will immediately lose airway images, which will delay rescue. Meanwhile, there are also methods of supplying an oxygen gas source into a body to increase the oxygen flow rate for directly blowing off contaminants adhered to the camera, or using a camera at a disposable laryngoscope blade inner cavity high-transparency closed end to capture airway images and collect secretion in light passing areas, but these decontamination methods can only blow off food residues blocking the camera, while they fail to remove blood or secretion adhered to the camera. The technical problem of video laryngoscope decontamination has been troubling the industry, and no desired solution has been found so far.

The inventor previously applied for the patent CN105212884A, which disclosed a video laryngoscope with a decontamination device. The video laryngoscope is composed of a disposable laryngoscope blade body, a tongue depressor, a laryngoscope blade inner cavity, a decontamination rod, a rotary shaft sleeve, a rotary shaft, a reset torsion spring, a scraper plate, and a limit clip plate. It uses a shift rod-rotary shaft type technical structure, and the rotary shaft rotates to drive the scraper plate to make a curve movement, thereby scraping contaminants off the laryngoscope. However, the scraper rod in such a rotary shaft structure is unable to make vertical parallel movement. It is clinically verified that it has the following shortcomings:

(1) Since the camera has a planar lens and the scraper plate makes a curve movement during the process of scraping contaminants off the camera, the scraper plate is unable to get tightly fitted with the camera, resulting in dead corners between the scraper plate and the camera and incomplete scraping, that is, contaminants cannot be completely scraped off the surface of the camera, to cause airway image blur when the camera captures airway images and an undesired decontamination effect.

(2) The shift rod-rotary shaft structure requires a distance between the shift rod and the laryngoscope handle so as to give a space for a hand to hold the laryngoscope handle and the shift rod to move. In application, the laryngoscope handle is held by a left hand and the left thumb pushes the decontaminating scraper rod to carry out decontamination under the action of forward and backward movement of the left thumb, while a catheter for tracheal intubation is held by the right hand to complete tracheal intubation. The clinical verification results have shown that, when the thumb pushes the shift rod to move, it will easily cause the laryngoscope to be unsteadily held, especially by female medical staff having inadequate grip strength. In a tracheal intubation operation, a laryngoscope is held by a left hand, and the laryngoscope blade is put into an oral cavity to gently lift the epiglottis upwards to expose the glottis, while a tracheal catheter is held by the right hand and inserted into the trachea. Two hands work together to fulfill their respective responsibilities.

By adding a guided decontamination device, the present invention enables a rubber hose on a decontamination scraper rod to get tightly fitted with the lens face of a camera, uses a reset spring to keep up-down parallel movement between a decontamination rod and the decontamination scraper rod, and can effectively scrape off blood or secretion adhered to the camera or regions where a video laryngoscope captures airway images, thereby achieving real-time observation and collection of airway images through the camera and ensuring the normal use of the video laryngoscope.

SUMMARY OF THE INVENTION

In order to make up for the technical defects of the video laryngoscope mentioned above, the present invention aims to provide a video laryngoscope with a guided decontamination device.

The invention discloses a video laryngoscope with a guided decontamination device. It comprises a laryngoscope handle and a video laryngoscope blade provided with a light source and a camera at the front end. The guided contamination device included is composed of a guide tube and a decontamination rod. The guide tube is fixed on the outer wall of the laryngoscope handle, and has its guiding angle in parallel to the end faces of the camera and the light source at the front end of the laryngoscope blade. The decontamination rod comes into a sliding fit with the guide tube, runs out from the bottom of the guide tube upwards, and has its front end bent to form a decontamination scraper rod. The decontamination scraper rod comes into a tight fit with the end faces of the camera and the light source at the front end of the laryngoscope blade. Preferably, the guide tube has its upper segment acting as a spring chamber, and its lower segment acting as a guide chamber, the diameter of the spring chamber is larger than that of the guide chamber, a reset spring is assembled in the spring chamber and the decontamination rod and the guide chamber are in a sliding fit with each other.

Preferably, the inner sidewall of the front end of the video laryngoscope blade is provided with a decontamination scraper rod guide groove where one end of the decontamination scraper rod is assembled. The decontamination scraper rod is guided through sliding fit in the decontamination scraper rod guide groove, and the decontamination scraper rod is parallel to the end faces of the camera and the light source to ensure a tight fit between the decontamination scraper rod and the end faces of the camera and the light source.

Preferably, a decontamination rod button is arranged at the upper end of the decontamination rod, and has one end arranged in the spring chamber and the other end exposed outside the spring chamber.

Preferably, the outer wall of the video laryngoscope blade is provided with a limit snap ring, which is movably inserted in the video laryngoscope blade to form a decontamination rod limit chamber between the limit snap ring and the outer wall of the video laryngoscope blade, and the decontamination rod is arranged movably in the decontamination rod limit chamber.

Preferably, the decontamination scraper rod is provided with a decontamination rubber hose.

Preferably, the laryngoscope handle is provided with a display screen connected with the camera.

Preferably, the decontamination rod is a metal wire with a diameter of 2 mm or so.

The present invention further provides a video laryngoscope with a guided decontamination device. The video laryngoscope comprises a laryngoscope handle and a disposable video laryngoscope blade. The disposable laryngoscope blade comprises a laryngoscope blade inner cavity high-transparency closed end for a camera to capture images and a light source to pass. It is characterized by further comprising the guided decontamination device composed of a guide tube and a decontamination rod. The guide tube is fixed on the outer wall of a tail end of the main body of the disposable video laryngoscope blade, and has its guiding angle in parallel to the end face of the laryngoscope blade inner cavity high-transparency closed end. The decontamination rod comes into a sliding fit with the guide tube, runs out from the bottom of the guide tube upwards, and has its front end bent to form a decontamination scraper rod. The decontamination scraper rod is tightly fitted with the end face of the laryngoscope blade inner cavity high-transparency closed end.

Preferably, the guide tube has its upper segment acting as a spring chamber, and its lower segment acting as a guide chamber, the diameter of the spring chamber is larger than that of the guide chamber, a reset spring is assembled in the spring chamber, and the decontamination rod and the guide chamber are in a sliding fit with each other.

Preferably, an extension arm is included. The disposable video laryngoscope blade comprises a laryngoscope blade inner cavity and a tongue depressor. The rear end of the laryngoscope blade inner cavity body is open, and the laryngoscope blade inner cavity is inserted on the extension arm.

Preferably, the sidewall of the front end face of the laryngoscope blade inner cavity is provided with a decontamination scraper rod guide groove where one end of a decontamination scraper rod is assembled. The decontamination scraper rod is guided through sliding fit in the decontamination scraper rod guide groove, and the decontamination scraper rod guide groove is parallel to the end face of the laryngoscope blade inner cavity high-transparency closed end to ensure tight fit between the decontamination scraper rod and the end face of the laryngoscope blade inner cavity high-transparency closed end.

Preferably, a decontamination rod button is arranged at the upper end of the decontamination rod, and has one end arranged in the spring chamber and the other end exposed outside the spring chamber.

Preferably, the outer wall of the disposable video laryngoscope blade is provided with a limit snap ring, which is movably inserted in the disposable video laryngoscope blade to form a decontamination rod limit chamber between the limit snap ring and the outer wall of the disposable video laryngoscope blade, and the decontamination rod is arranged movably in the decontamination rod limit chamber.

Preferably, the decontamination scraper rod is provided with a decontamination rubber hose.

Preferably, the laryngoscope handle is provided with a display screen connected with the camera.

Preferably, the decontamination rod is a metal wire with a diameter of 2 mm or so.

A preferred manufacturing method of the decontamination rod includes bending a metal wire with high strength and a diameter of 2 mm or so to form a decontamination scraper rod. The decontamination rod, formed by bending a metal wire, has a small volume, saves space, exerts no influence on operation vision, and is low in manufacturing cost, simple to assemble and convenient for industrial mass production.

The assembling steps include (1) fitting a decontamination rubber hose on a decontamination scraper rod; (2) running a decontamination rod out from the bottom of a guide tube upwards, with one end of the decontamination scraper rod assembled in a decontamination scraper rod guide groove; (3) arranging a limit snap ring on the outer wall of a video laryngoscope blade or the outer wall of a disposable video laryngoscope blade and movably arranging the decontamination rod in a decontamination rod limit chamber; (4) fitting a reset spring on the decontamination rod and assembling in a spring chamber; and (5) installing a decontamination rod button at the upper end of the decontamination rod.

In application, the main body of the disposable video laryngoscope blade is movably inserted in an extension arm, and the guide tube and a laryngoscope handle are movably fitted so that an operator can hold the guide tube and the laryngoscope handle together as a whole in the hand to facilitate operation, and vertically press down the decontamination rod button with the left thumb to enable linkage between the decontamination rod and the decontamination scraper rod, thereby scraping secretion off the end faces of the camera and the light source at the front end of the laryngoscope blade or the end face of the laryngoscope blade inner cavity high-transparency closed end, to allow the camera for real-time capture of airway images.

The present invention has the following technical advantages:

(1) The decontamination scraper rod is kept to move up and down in parallel to the end faces of the camera and the light source at the front end of the laryngoscope blade or the end face of the laryngoscope blade inner cavity high-transparency closed end under the guiding action of the guide tube, so that the decontamination scraper rod comes into a tight fit with the end faces of the camera and the light source at the front end of the laryngoscope blade or the end face of the laryngoscope blade inner cavity high-transparency closed end, to ensure precise and reliable decontamination and a clear decontamination effect.

(2) The decontamination rod is pushed to move up and down by a thumb which operates and moves smoothly, and is flexible and labor-saving, without influencing the stability of the laryngoscope held by a hand.

Figure 1:
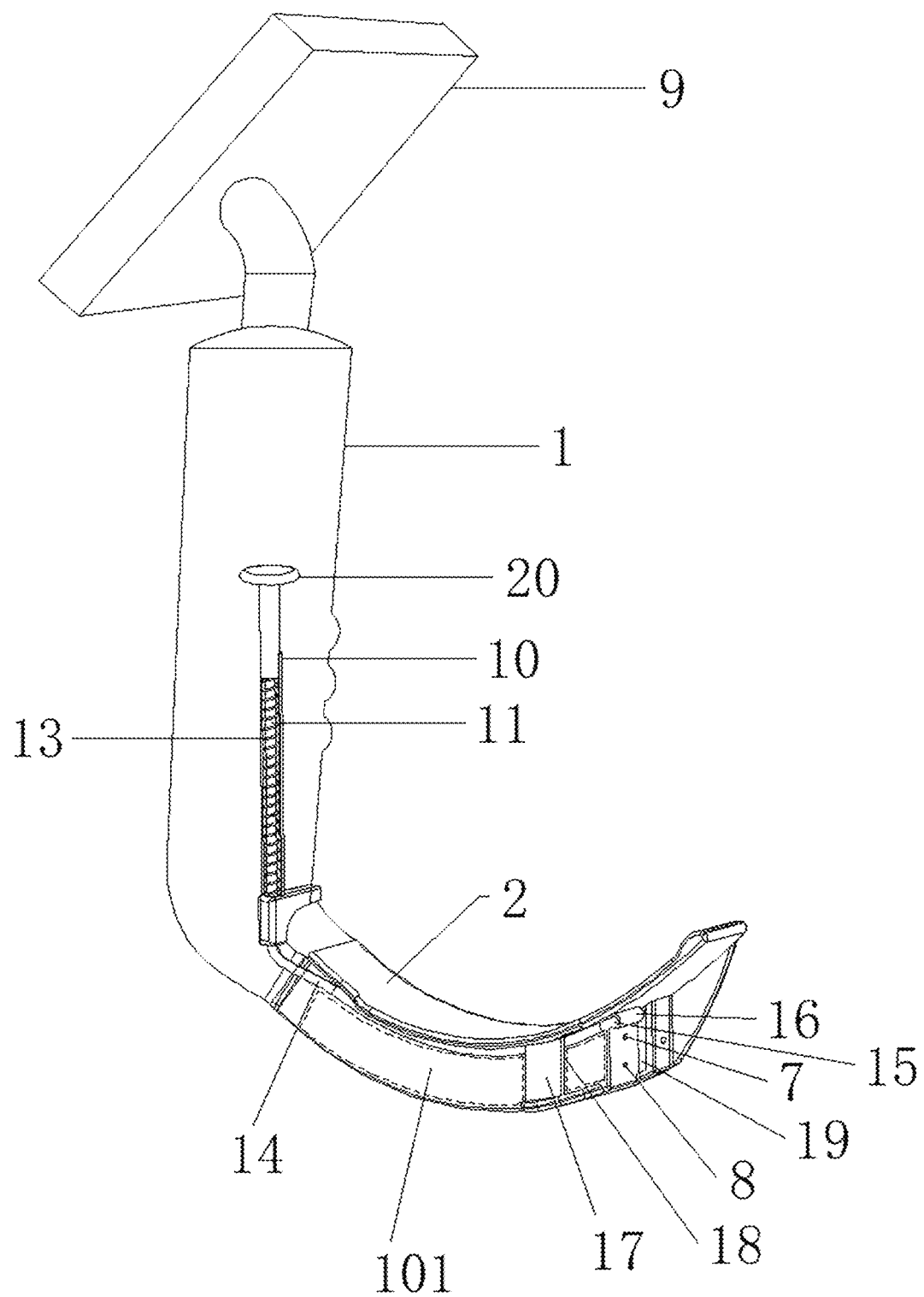
FIG. 1 is a schematic diagram of the overall structure of a video laryngoscope with a guided decontamination device in the invention.

Laryngoscope handle 1, video laryngoscope blade 2, disposable video laryngoscope blade 3, laryngoscope blade inner cavity 4, laryngoscope blade inner cavity high-transparency closed end 5, tongue depressor 6, light source 4, camera 8, display screen 9, guide tube 10, spring chamber 11, guide chamber 12, reset spring 13, decontamination rod 14, decontamination scraper rod 15, decontamination rubber hose 16, limit snap ring 17, decontamination rod limit chamber 18, decontamination scraper rod guide groove 19, decontamination rod button 20, extension arm 101.

DETAILED DESCRIPTION OF THE EMBODIMENTS

Example 1

Figure 4:
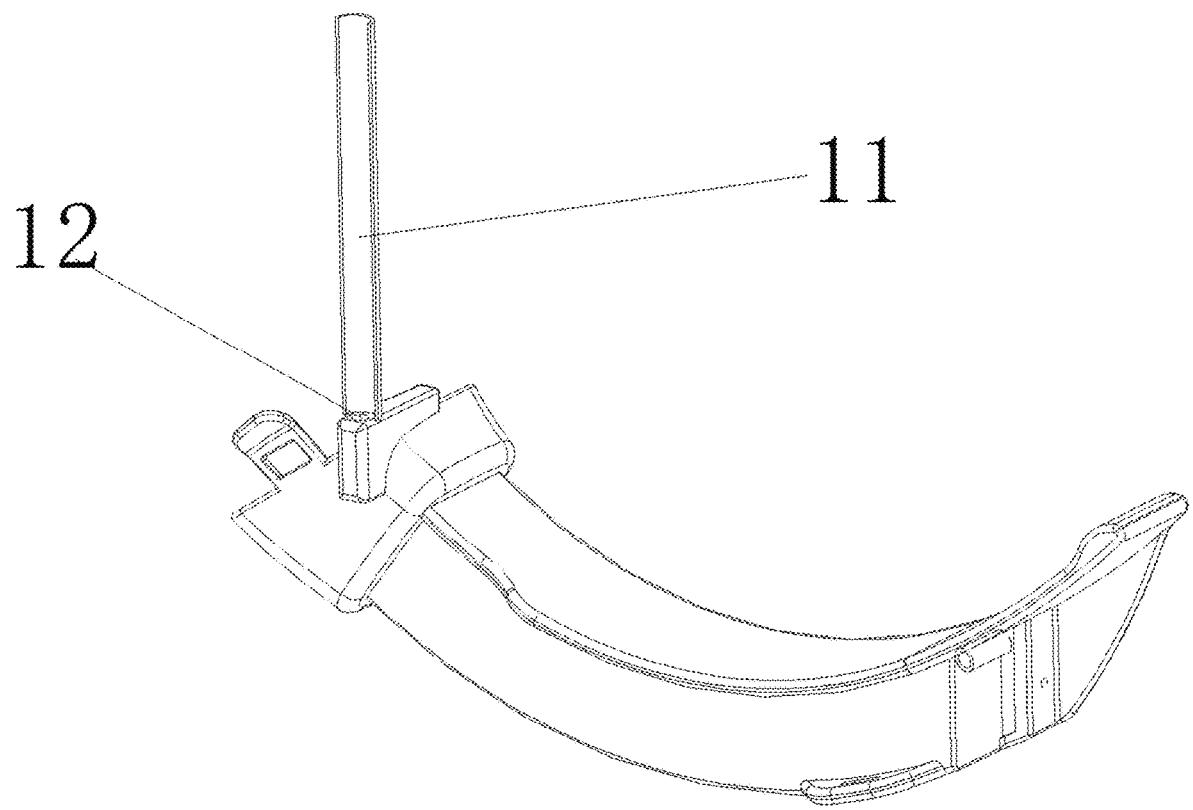
FIG. 4 is a schematic diagram of a separated guide tube in the invention.

As shown in FIG. 1 and FIG. 4, a video laryngoscope with a guided decontamination device comprises a laryngoscope handle 1 and a video laryngoscope blade 2. The front end of the video laryngoscope blade 2 is equipped with a light source 7 and a camera 8. The laryngoscope handle 1 is equipped with a display screen 9 connected with the camera 8. The guided decontamination device included is composed of a guide tube 10 and a decontamination rod 14. The guide tube 10 is fixed on the outer wall of the laryngoscope handle 1, and has its guiding angle in parallel to the end faces of the camera 8 and the light source 7 at the front end of the laryngoscope blade. The decontamination rod 14 comes into a sliding fit with the guide tube 10. The guide tube 10 has its upper segment acting as a spring chamber 11, and its lower segment acting as a guide chamber 12, the diameter of the spring chamber 11 is larger than that of the guide chamber 12. A reset spring 13 is assembled in the spring chamber 11. The decontamination rod 14 runs out from the bottom of the guide tube 10 upwards, and has its front end bent to form a decontamination scraper rod 15. The decontamination scraper rod 15 comes into a tight fit with the end faces of the light source 7 and the camera 8 at the front end of the laryngoscope blade. The inner sidewall of the front end of the video laryngoscope blade 2 is provided with a decontamination scraper rod guide groove 19 where one end of the decontamination scraper rod 15 is assembled. The decontamination scraper rod 15 is guided through sliding fit in the decontamination scraper rod guide groove 19, and the decontamination scraper rod guide groove 19 is parallel to the end faces of the camera 8 and the light source 7 to ensure a tight fit between the decontamination scraper rod 15 and the end faces of the camera 8 and the light source 7. A decontamination rod button 20 is arranged at the upper end of the decontamination rod 14 and has one end arranged in the spring chamber 11 and the other end exposed outside the spring chamber 11. The outer wall of the video laryngoscope blade 2 is provided with a limit snap ring 17, which is movably inserted in the video laryngoscope blade 2 to form a decontamination rod limit chamber 18 between the limit snap ring 17 and the outer wall of the video laryngoscope blade 2. The decontamination rod 14 is arranged movably in the decontamination rod limit chamber 18. The decontamination scraper rod 15 is provided with a decontamination rubber hose 16. The decontamination rod 14 is a metal wire with a diameter of 2 mm or so.

Example 2

Figure 2:
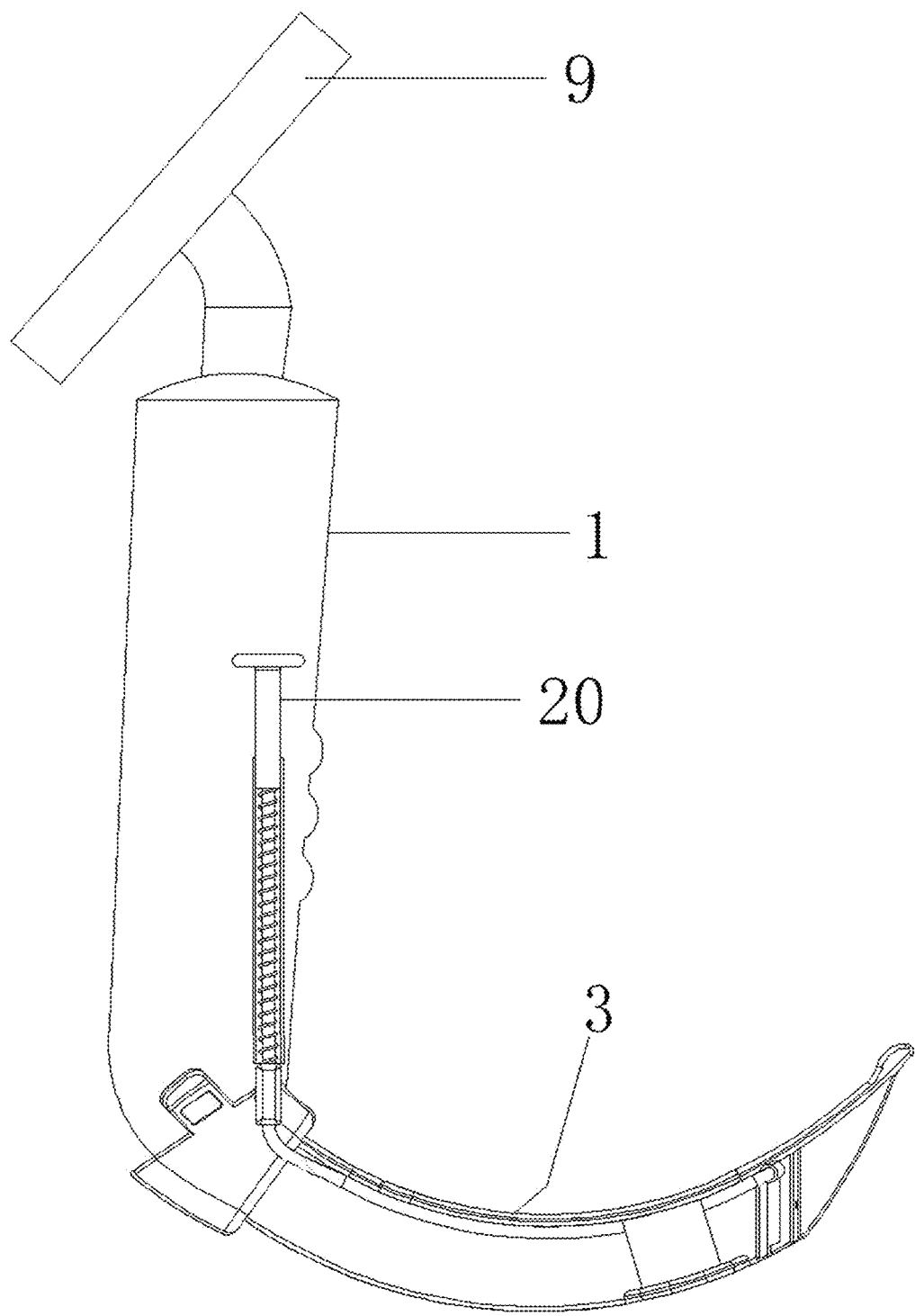
FIG. 2 is a schematic diagram of the guided decontamination device in the invention.
Figure 3:
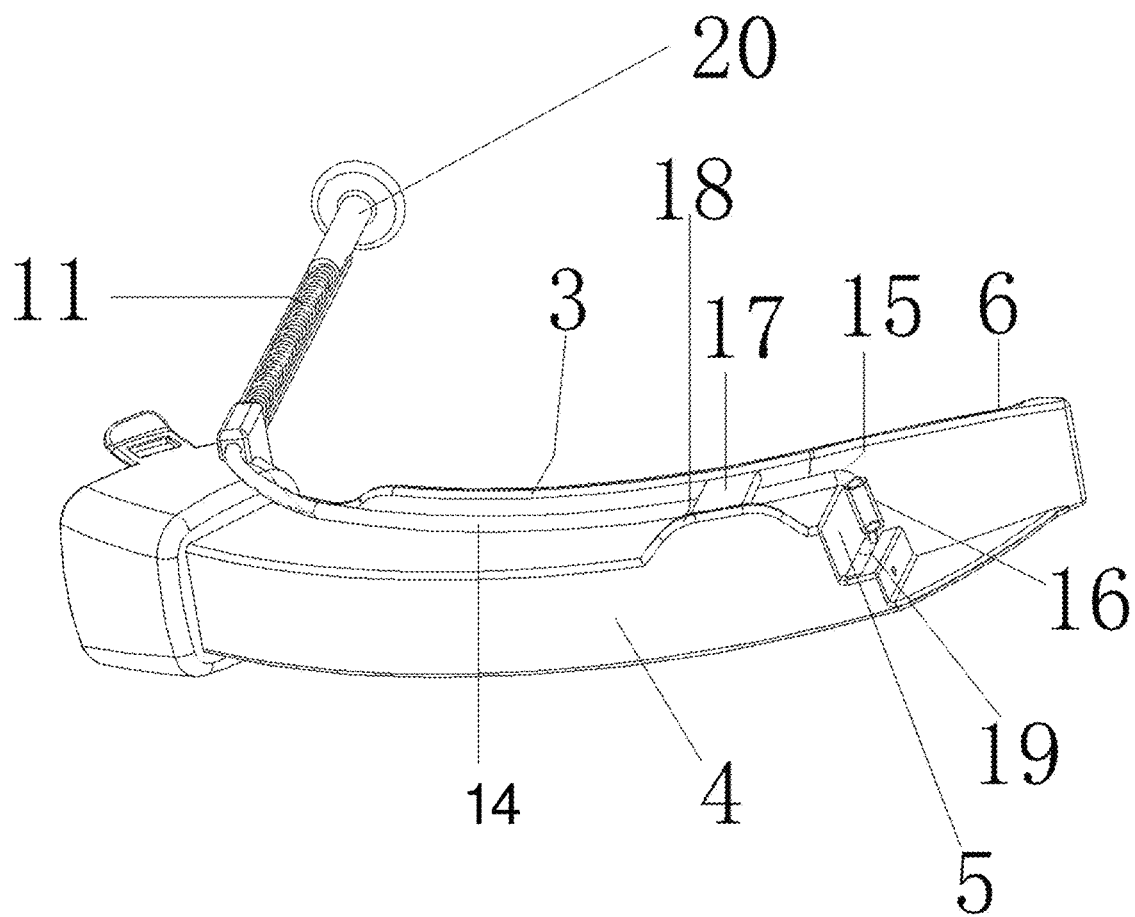
FIG. 3 is a schematic diagram of the main body of a disposable laryngoscope blade with a guided decontamination device in the invention.

As shown in FIG. 2, FIG. 3 and FIG. 4, a video laryngoscope with a guided decontamination device comprises a laryngoscope handle 1 and a disposable video laryngoscope blade 3. The disposable video laryngoscope blade 3 comprises a laryngoscope blade inner cavity high-transparency closed end 5 for a camera to capture images and a light source to pass. The laryngoscope handle 1 is provided with a display screen 9 connected with a camera 8. The guided decontamination device included is composed of a guide tube 10 and a decontamination rod 14. The guide tube 10 is fixed on the outer wall of a tail end of the main body of the disposable video laryngoscope blade 3, and has its guiding angle in parallel to the end face of the laryngoscope blade inner cavity high-transparency closed end 5. The decontamination rod 14 comes into a sliding fit with the guide tube 10. The guide tube 10 has its upper segment acting as a spring chamber 11, and its lower segment acting as a guide chamber 12, the diameter of the spring chamber 11 is larger than that of the guide chamber 12, and a reset spring 13 is assembled in the spring chamber 11. The decontamination rod 14 runs out from the bottom of the guide tube 10 upwards, and has its front end bent to form a decontamination scraper rod 15. The decontamination scraper rod 15 is tightly fitted with the end face of the laryngoscope blade inner cavity high-transparency closed end 5. An extension arm 101 is further included. The disposable video laryngoscope blade 3 comprises a laryngoscope blade inner cavity 4 and a tongue depressor 6. The rear end of the laryngoscope blade inner cavity 4 is open, and the laryngoscope blade inner cavity 4 is inserted on the extension arm 101. The sidewall of the front end face of the laryngoscope blade inner cavity 4 is provided with a decontamination scraper rod guide groove 19 where one end of a decontamination scraper rod 15 is assembled. The decontamination scraper rod 15 is guided through sliding fit in the decontamination scraper rod guide groove 19, and the decontamination scraper rod guide groove 19 is parallel to the end face of the laryngoscope blade inner cavity high-transparency closed end 5 to ensure tight fit between the decontamination scraper rod 15 and the end face of the laryngoscope blade inner cavity high-transparency closed end 5. A decontamination rod button 20 is arranged at the upper end of the decontamination rod 14, and has one end arranged in the spring chamber 11 and the other end exposed outside the spring chamber 11. The outer wall of the video laryngoscope blade 2 is provided with a limit snap ring 17, which is movably inserted on the video laryngoscope blade 2 to form a decontamination rod limit chamber 18 between the limit snap ring 17 and the outer wall of the video laryngoscope blade 2, and the decontamination rod 14 is arranged movably in the decontamination rod limit chamber 18. The decontamination scraper rod 15 is provided with a decontamination rubber hose 16. The decontamination rod 14 is a metal wire with a diameter of 2 mm or so.

What is claimed is:
1. A video laryngoscope comprising:
    a laryngoscope handle;
    a video laryngoscope blade, wherein a front end of the video laryngoscope blade is equipped with a light source and a camera; and a guided decontamination device that includes a guide tube and a decontamination rod, wherein:

the guide tube is fixed on an outer wall of the laryngoscope handle;

the decontamination rod comes into a sliding fit with the guide tube, extends upward from a bottom of the guide tube, and has a front end bent to form a decontamination scraper rod;

the decontamination scraper rod is fit with end faces of the camera and the light source at the front end of the video laryngoscope blade;

the guide tube has an upper segment that is used as a spring chamber, and a lower segment that is used as a guide chamber;

a diameter of the spring chamber is larger than that of the guide chamber, a reset spring is assembled in the spring chamber, and the decontamination rod and the guide chamber are in a sliding fit with each other;

wherein a inner sidewall of the front end of the video laryngoscope blade is provided with a decontamination scraper rod guide groove where one end of the decontamination scraper rod is assembled;

the decontamination scraper rod extends through a sliding fit in the decontamination scraper rod guide groove, and the decontamination scraper rod is parallel to the end faces of the camera and the light source to achieve a fit between the decontamination scraper rod and the end faces of the camera and the light source;

an outer wall of the video laryngoscope blade is provided with a limit snap ring, which is movably inserted in the video laryngoscope blade to form a decontamination rod limit chamber between the limit snap ring and the outer wall of the video laryngoscope blade; and the decontamination rod is arranged movably in the decontamination rod limit chamber.

2. The video laryngoscope according to claim 1, wherein a decontamination rod button is arranged at an upper end of the decontamination rod, and has one end arranged in the spring chamber and another end exposed outside the spring chamber.

3. The video laryngoscope according to claim 1, wherein the decontamination scraper rod is provided with a decontamination rubber hose.

4. The video laryngoscope according to claim 3, wherein the laryngoscope handle is provided with a display screen connected with the camera.

5. The video laryngoscope according to claim 4, wherein the decontamination rod is a metal wire with a diameter of 2 mm.

6. A video laryngoscope comprising:
a laryngoscope handle;
a disposable video laryngoscope blade, wherein the disposable video laryngoscope blade comprises a laryngoscope blade inner cavity high-transparency closed end for a camera to capture images and a light source to pass;
an extension arm; and
a guided decontamination device that includes a guide tube and a decontamination rod, wherein:

the guide tube is fixed on an outer wall of a tail end of a main body of the disposable video laryngoscope blade;

the decontamination rod comes into a sliding fit with the guide tube, extends upward from a bottom of the guide tube, and has a front end bent to form a decontamination scraper rod;

the decontamination scraper rod is fit with an end face of the laryngoscope blade inner cavity high-transparency closed end;

the guide tube has an upper segment that is used as a spring chamber, and a lower segment that is used as a guide chamber;

a diameter of the spring chamber is larger than that of the guide chamber, a reset spring is assembled in the spring chamber, and the decontamination rod and the guide chamber are in a sliding fit with each other;

the disposable video laryngoscope blade includes a laryngoscope blade inner cavity and a tongue depressor, a rear end of the laryngoscope blade inner cavity being open, and the laryngoscope blade inner cavity being inserted in the extension arm;

a sidewall of a front end face of the laryngoscope blade inner cavity is provided with a decontamination scraper rod guide groove where one end of the decontamination scraper rod is assembled;

the decontamination scraper rod extends through a sliding fit in the decontamination scraper rod guide groove, and the decontamination scraper rod guide groove is parallel to the end face of the laryngoscope blade inner cavity high-transparency closed end to achieve a fit between the decontamination scraper rod and the end face of the laryngoscope blade inner cavity high-transparency closed end;

a decontamination rod button is arranged at an upper end of the decontamination rod, and the decontamination rod has one end arranged in the spring chamber and another end exposed outside the spring chamber;

an outer wall of the disposable video laryngoscope blade is provided with a limit snap ring, which is movably inserted on in the disposable video laryngoscope blade to form a decontamination rod limit chamber between the limit snap ring and the outer wall of the disposable video laryngoscope blade; and the decontamination rod is arranged movably in the decontamination rod limit chamber.

7. The video laryngoscope according to claim 6, wherein the decontamination scraper rod is provided with a decontamination rubber hose.

8. The video laryngoscope according to claim 7, wherein the laryngoscope handle is provided with a display screen connected with the camera.

9. The video laryngoscope according to claim 8, wherein the decontamination rod is a metal wire with a diameter of 2 mm.

* * * * *